United States Patent [19]

Birnbach et al.

[11] Patent Number: 4,653,855
[45] Date of Patent: Mar. 31, 1987

[54] APPARATUS AND PROCESS FOR OBJECT ANALYSIS BY PERTURBATION OF INTERFERENCE FRINGES

[75] Inventors: Curtis Birnbach, Bronx; Jay Tanner, Nesconset, both of N.Y.

[73] Assignee: Quantum Diagnostics Ltd., Hauppauge, N.Y.

[21] Appl. No.: 658,870

[22] Filed: Oct. 9, 1984

[51] Int. Cl.$^4$ .......................... G02B 27/00; G01B 9/02
[52] U.S. Cl. .................... 350/163; 350/320; 356/345
[58] Field of Search ............... 350/3.6, 163, 320, 1.1; 356/345, 354, 360, 361; 250/341, 493.1, 343

[56] References Cited

U.S. PATENT DOCUMENTS 4,459,027  7/1984  Kafvi et al. .................... 356/128

Primary Examiner—Bruce Y. Arnold
Attorney, Agent, or Firm—Ostrolenk, Faber, Gerb & Soffen

[57] ABSTRACT

Objects to be examined, such as tissue or any cellular or crystalline material, e.g. semiconductor wafers, are placed in a region of confluence of two interfering coherent beams of radiation which are at the same frequency and phase and at a frequency to which the object is semi-transparent. The beams are produced by separate sources or by refraction by a Fresnel biprism or any other interferometer structure. An off-axis parabolic reflection system is also disclosed. The interference fringe phase and amplitude perturbation produced by the object is detected and examined to derive information regarding physical properties of the object or abnormalities in its structure. Such abnormalities, as fractures or latent stresses in a semi-conductor wafer or the presence of tumors in biological tissue can be determined. Chemical characteristics of living tissue is determined by sweeping the frequency of the coherent radiation over a band which includes the absorption bands of given chemicals such as hydrogen, oxygen, sodium, and other materials which are representative of the structure of living tissue. The frequencies employed may be in the microwave band, millimeter band or higher.

13 Claims, 13 Drawing Figures

APPARATUS AND PROCESS FOR OBJECT ANALYSIS BY PERTURBATION OF INTERFERENCE FRINGES

BACKGROUND OF THE INVENTION

This invention relates to the analysis of objects, including living tissue, by observing the perturbation of interference fringes between two interfering coherent beams of radiation in the object space.

Instruments for the non-invasive analysis of the interiors of bodies, particularly biological tissue, are well known. By biologic tissue is meant living or dead tissue and the like. For example, x-ray apparatus is commonly used for the examination of both living tissue and inert materials. The use of x-rays for examination of living tissue, particularly human beings, is hazardous because x-rays are ionizing radiation. Therefore, the use of x-ray examination is limited and the resolution which can be obtained through x-ray examination is limited because of dosage considerations.

The use of radioactive material is also fairly common for the examination of living tissue where the material is injected or ingested or otherwise applied to the living tissue. The tissue is then scanned to determine the concentation pattern of the radioactive material. The use of such diagnostic techniques again involves the use of ionizing radiation and the use and resolution obtained by the measurement is limited.

Many other systems are known for the non-invasive testing of human tissues, such as nuclear magnetic resonance techniques (NMR). Nuclear magnetic resonance techniques are in growing use but the apparatus is extremely expensive and requires very long exposure times, for example 8–10 seconds, during which a patient can not move. Furthermore, the use of NMR equipment requires the patient to be placed in a long tunnel defining the magnet which has adverse psychological attributes.

Many other non-invasive examination mechanisms including those employing ultrasound are also known, each having well known disadvantages.

BRIEF DESCRIPTION OF THE INVENTION

In accordance with the present invention, non-ionizing radiation is employed for the examination of the interior of objects to be analyzed. More particularly, and in accordance with the invention, two coherent beams of radiation are produced and are directed relative to one another such that their wavefronts interact in a region of confluence of the beams wherein an interference fringe pattern is produced. The frequency employed for the coherent radiation can be from microwave range through the millimeter range and higher into the optical range. The frequency selected is one at which the object to be analyzed is at least partly transparent. The object to be analyzed is then placed in the region of confluence of the two beams so that the object will distort the interference fringe pattern which is produced by the interfering wave fronts of the two beams. In effect, the interference field is employed as an active grating with an adjustable period which provides an adjustment for the limiting spatial resolution for the system.

The nature of the interference pattern change or perturbation is related to particular selected characteristics of the object being examined. By way of example, in the analysis of biological tissue, the presence of a mass or region of thickened tissue will produce a perturbation in the interference fringe pattern which would not occur in a normal tissue sample which does not include such a thickened region.

In another use of the novel apparatus, still applied to the study of biological tissue, the frequency band of the coherent interfering beams is swept over a relatively narrow range to include one or more absorption bands of such elements and compounds such as hydrogen, water, salts, oxygen, calcium, iron and sodium. The presence of these elements and compounds will produce characteristic changes in the interference fringe perturbation when that particular frequency is reached during the sweep of the coherent beam frequency. This, in turn, will reveal physiochemical or physiological conditions representing an excess of or dimished quantities of the element in question due to certain pathological processes. Thus, the analysis of the content of hydrogen, water, oxygen, calcium, iron and sodium and other elements has a known relationship to pathological conditions in the use of NMR equipment and the same information can be obtained through the novel apparatus of the present invention.

When applied to human tissue, the frequencies used are preferably in the microwave to millimeter range, although higher frequencies may be used. Energy is applied for a short time to prevent excessive heating of the tissue. By way of example, the beam frequency can be varied, as by stepping or sweeping through a given frequency range which contains the absorption frequencies being investigated. As the frequency reaches a desired absorption frequency, it can dwell for a short time, for example, of the order of a millisecond, and is thereafter stepped or swept to the next absorption band of interest. One full cycle lasts less than about 20 milliseconds, whereby the measurement is unaffected by heart movement or body movement of a patient. A cycle time of less than about 30 milliseconds is needed to display human heart readings without being affected by the contractions and expansions of the heart. The frequency range which is input is preferably from about 5 gigahertz to 500 gigahertz which will contain the relevant absorption bands presently known to us. A single cycle is believed to be sufficient to gather the data needed for an examination given an adequate source.

For examination of organic matter, the frequency sweep and dwell time can be adjusted, depending on the thermal sensitivity and absorption bands of interest in the sample. During the frequency sweep, data can be gathered on the fringe perturbation produced outside of the absorption band being examined. That data can then be "subtracted" from the data obtained at an absorption band of interest, thereby to produce an enhanced picture of the distortion produced at one or more absorption bands of interest. By pulsing the energy, undesired heating effects are reduced.

Frequencies outside of the millimeter band can also be used for analysis of other objects. By way of example, internal stress or fractures in a wafer of monocrystaline silicon can be determined by employing a source of coherent radiation having a frequency in the infrared range, particularly an infrared laser source having a wavelength of greater than 1.2 microns. The 1.32 micron line of an ND-YAG laser is very useful for semiconductor analysis. A tunable dye laser could also be used; this would allow sweeping past the absorption bands. An ND-YAG laser would be useful as a pump for the dye laser, sweeping from the 1.064 um line to further into the infrared band. There are numerous inexpensive sources available. The interference fringe patterns can then be imaged on a suitable infrared vidicon or the like. Other monocrystalline, polycrystalline or amorphous silicon objects can also be examined by selection of appropriate frequencies. Obviously, objects of other materals can similarly be examined.

Numerous radiation sources can be employed with the present invention. For example, when employing microwave frequencies, a single microwave generator can be employed. Its output is then split and delivered to spaced microwave antenna which produce converging coherent radiation beams which converge on the object to be examined. One leg preferably contains a precision phase matching apparatus.

Alternatively, the output of a single microwave radiation source can be applied to a Fresnel biprism implemented in a material of an appropriate refractive index for the frequency in use. The biprism will produce two output beams beams of coherent radiation which converge toward one another. Such Fresnel biprisms are known and have been used for educational demonstrations in the visible light range but have not been used for any microwave, millimeter wave or infrared application. In a microwave or millimeter wave application, the biprism should be made of a material such as polytetrafluoroethylene (Teflon) which is semi-transparent and refractive at those frequencies. Quartz Fresnel biprisms can be used for an infrared, visible, or ultraviolet source of radiation.

Another useful source of the beams of coherent light which have a region of interfering confluence can be derived from an interferometer, for example, a Mach-Zehnder interferometer.

A useful source of input radiation is provided when a microwave source is directed toward an off-axis parabola which transforms the spherical wavefronts of the source output into parallel wavefronts. The parallel wavefronts are then applied to a Fresnel biprism which develops the convergent beams of coherent radiation which converge in an interference region containing the object to be examined. This is the preferred embodiment of the invention for medical applications since it enables use of equipment which is compatible in size with existing x-ray equipment and peripherals, and x-ray rooms in hospitals.

While a significant advantage of the invention is to avoid the use of ionizing radiation, sources of ionizing radiation (up to about 10 KEV) can, if desired, by employed in the manner disclosed for the present invention. A monocrystalline interferometer or a Wolter type grazing incidence mirror system may be employed to produce the interference fringe pattern.

The detectors for detecting the signal containing the perturbed interference fringes can be any desired known infrared, visible, ultraviolet, microwave, or millimeter wave detector. By way of example, microwave interference fringes can be measured by appropriate modification of known traveling wave modulators to produce a traveling wave detector in which microwave radiation modulates a light beam. It is also possible to use phased array receptor systems.

Other receivers can consist simply of a film having a silver halide modified to be responsive to the microwave radiation or to the particular radiation frequency employed. Solid state detectors and liquid crystal detectors can also be used.

The output information can be compiled and analyzed by any desired well known process for analyzing and presenting such information. By way of example, the information produced can be scanned and applied, element by element, to a computer to process the information and to produce an output image of the fringe pattern pertubations. Image subtraction techniques can be used. These may be obtained by comparing the fringe pattern which is produced without the object in the object space to the perturbed pattern or by comparing the perturbation of the sample to the perturbation caused by a standard sample of the subject or by comparing (subtracting) the perturbations at different frequencies. The perturbation patterns can then be presented in two-dimensional or three-dimension form. Thus, it is possible, for example, to employ techniques similar to those used in CAT Scans or holographic reconstruction to produce the effect of a planar x-ray with information in two or three dimensions.

The perturbation of fringes as a result of interaction between the radiation waves and the object matter will consist of changes in fringe position and in light absorption.

The displacement of the fringe position for a given frequency will be covered by Snells' law:

$$n \sin \theta = n' \sin \theta',$$

where n and n' are the indices of refraction in a refracting region of changing index of refraction, and $\theta$ and $\theta'$ are the angles of incidence in the medias having indices n and n', respectively. The index of refraction n may change to n' in step fashion, or in continuous matter at a constant or variable rate of change.

The fringe intensity pertubation is governed by the Lambert-Beer Law of Absorption:

$$I/Io = e^{-aL},$$

where:
I = Incidence intensity
Io = Transmitted intensity
$a$ = Linear absorption coefficient
L = Distance transversed through media.

DETAILED DESCRIPTION OF THE DRAWINGS

Figure 1:
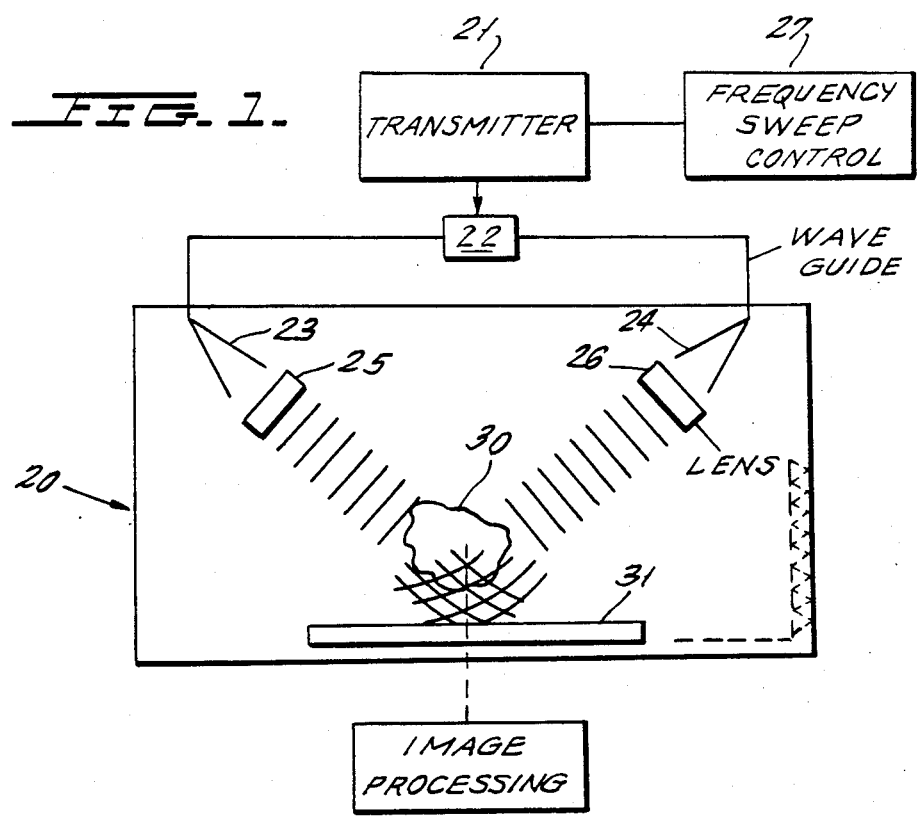
FIG. 1 schematically illustrates a first embodiment of the invention in which two microwave antenna produce interfering, convergent beams in an object area containing an object to be examined.

Referring first to FIG. 1, there is shown therein a schematic top view of a treatment room 20 adapted for carrying out the present invention. The walls of the room may be microwave shielded by conventional microwave absorbing pyramids which line the surfaces thereof. A microwave generator 21 is disposed exteriorly of room 20 and is connected to a signal splitter 22 which connects the energy of generator 21 through appropriate wave guides, to microwave antenna 23 and 24. Appropriate microwave lenses 25 and 26 are disposed in front of the output of antenna 23 and 24, respectively. A suitable frequency sweep control circuit 27 is connected to the transmitter 21. In designing the antenna 23 and 24, a millimeter wave operating frequency is preferred. This will reduce room size and apparatus size. According to the Nyquist criterion, a small wavelength is preferred for better spatial resolution so that for the millimeter band, it is preferred to employ a frequency of from 5–500 gigahertz. Preferably, the room and apparatus is temperature stabilized to avoid frequency drift.

The generator 21 and frequency sweep control 27, in a typical embodiment of the invention, produce a millimeter wave output from antenna 23 and 24 at a frequency which can step from absorption band to absorption band over a range of 5 gigahertz to 500 gigahertz. Typical absorption bands can be found in the literature, or can be experimentally determined. Oxygen ($O_2$), for example, has two well defined absorption peaks, one at 60 gigahertz and a second at 119 gigahertz. Water also has two absorption peaks, one at about 21 gigahertz and the other at 183 gigahertz. Other absorption bands are well known for other materials. The output pulse at a given absorption band will have any desired shape and duration. The duration of a given pulse is preferably less than one millisecond with a sharp rise and fall shape. The deuration of a full cycle in which each of a plurality of absorption bands and/or standard frequency samples are taken in less than about 30 milliseconds.

Figure 2:
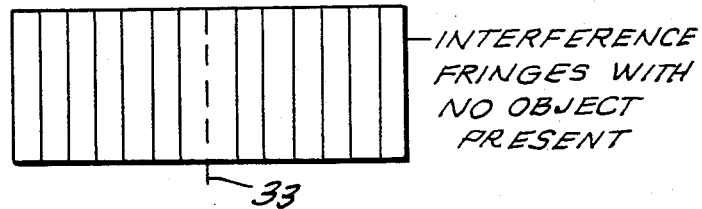
FIG. 2 shows the interference fringes which are produced in the apparatus of FIG. 1 when no object is present in the region of confluence of the two beams.

The antenna 23 and 24 are directed toward an object 30, which can, for example, be a tissue sample or a human being, with the object 30 being located in an area of confluence of the wavefronts of the two beams coming from lenses 25 and 26. Consequently, the tissue 30, which is semi-transparent and refractive to the radiation of the converging beams from antenna 23 and 24, will cause pertubations in the interferenece pattern which is produced at this overlapping area. By way of example, in the absence of object 30, interference fringes are produced, as shown in FIG. 2, whereas the object 30, when illuminated at a given frequency, causes the perturbed interference fringes shown in FIG. 3. The frequency of the radiation illuminating the object 30 may then be varied, which includes stepping or switching from standard frequencies and absorption frequencies with a single sweeping cycle.

The interference fringes which are produced are detected by a conventional microwave detector 31, which can be any desired type of two-dimensional detector, such as a traveling wave detector or phased array receptor system. It is also possible simply to use a film which is sensitive to the wavelength of the microwave radiation which is used or a solid state detector or liquid crystal detector.

The output of detector 31 can be digitized by any appropriate digitizing system well-known in the art and the image produced can then be computer-processed in any desired manner. By way of example, it is possible to display the perturbation caused by the presence of object 30 on the interference pattern at different illumination frequencies in an either two-dimensional or three-dimensional display. The display can also be a subtracted display in which only the perturbation caused at a given frequency is displayed in an enhanced manner.

Figure 3:
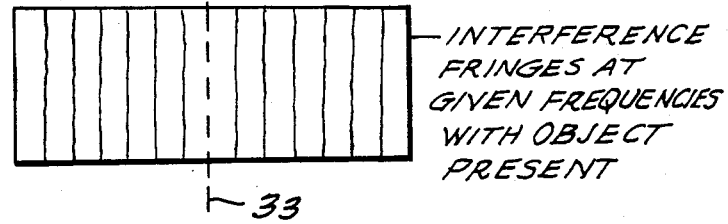
FIG. 3 shows the interference fringe pattern which is produced when an object is present in the object space of FIG. 1.

As shown in FIG. 3, the interference fringes will be perturbed differently about the two sides of the center line 33. The perturbations will be related to the characteristics of the object 30 and will be related, for example, to the frequency at which the interference fringe pattern of FIG. 3 was measured. For example, a unique perturbance pattern (to the object) will be produced when the microwave frequency is in the frequency absorption band of given elements. This makes it then possible to plot the concentration of elements of the volume of the object being examined by superposition of several images, each at a different frequency; the attenuated elements in each image representing the desired information. This can produce useful information related, for example, to the presence of tumorous masses and the like which would be particularly defined by the concentrations of various elements or compounds. Such abnormal and normal patterns are known in NMR processing techniques or can be derived experimentally.

In particular, the phase and amplitude and orientation information regarding the object 30 will be present in the fringe distortion, and this informatin can be derived from the fringe patterns in any desired manner. Note that the invention, in essence, employs the interference field as an active grating. Any interferometer can be used as a source of interference fringes.

Figure 4:
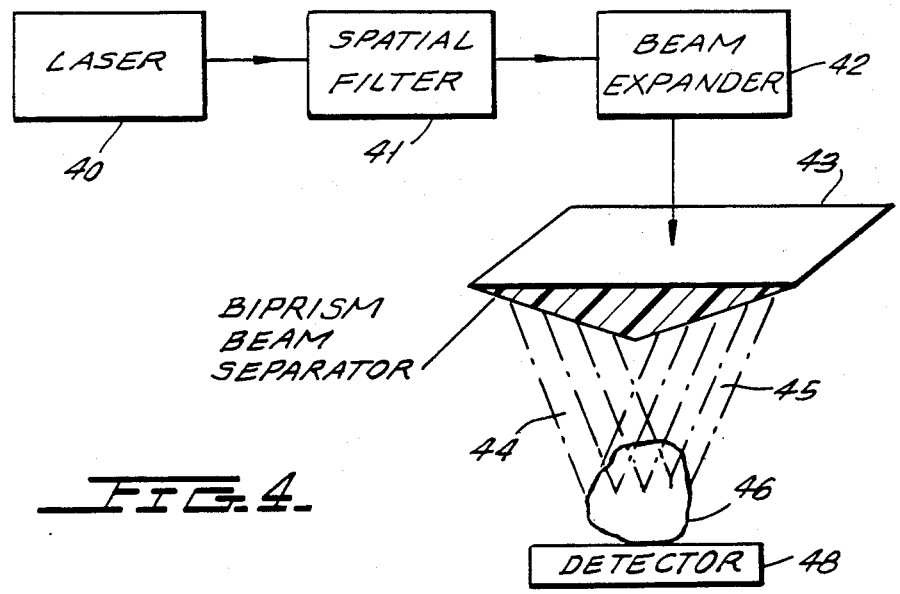
FIG. 4 is a schematic illustration of a second embodiment of the invention in which a Fresnel biprism beam separator is employed.

FIG. 4 shows another embodiment of the invention in which the apparatus is simplified and is operated from an infrared laser, rather than a microwave source. Note, however, that a maser or any other laser source can be used as well. Thus, in FIG. 4, a conventional infrared laser 40 is shown, which produces an output through a spatial filter 41 which removes noise and produces a high quality signal for the output radiation. The coherent beam output of the spatial filter 41 is then applied to a beam expander 42, which can be a suitable infrared lens, and is then applied to a quartz Fresnel biprism 43. Biprism 43 will produce two converging output beams 44 and 45 from the single input beam from the beam splitter 42. Note that prism 43 is shown in perspective view in FIG. 4 and is a rectangular prism. The prism angles are approximately 1°, 178° and 1°. These angles can vary depending on the required field of view, depth of field and size of object to be examined.

The two output beams 44 and 45 converge toward one another and interfere with one another in an object space containing an object 46. Consequently, the presence of the object 46, which is semi-transparent and refractive to the infrared radiation produced by laser 40, will perturb the interference fringe pattern due to hidden or latent or apparent discontinuities within the object 46 or on its surface. The radiation containing the perturbed interference fringe pattern proceeds toward the detector 48. Detector 48 may consist of any desired means to convert the radiation pattern to visible light and may then apply the light to a ground glass screen which can be photographed. The perturbed light pattern can also be optoelectrically converted for display on a cathode ray tube. The perturbed fringe pattern, as monitored by detector 48, may also be processed as described in connection with FIGS. 1, 2 and 3.

Note that a biprism such as biprism 43 could be used for processing energy in the microwave and millimeter ranges where the biprism would then be of polytetrafluorethylene (Teflon) which is semi-transparent and has a usable index of refraction at those frequencies.

In the embodiment of FIG. 4, the object 46 being examined can be a material such as a monocrystaline silicon wafer being examined for hidden fractures and latent stresses. The occurence of a fracture or stress in the wafer would be revealed by a given perturbation from the pattern which would be produced from an unstressed and unfractured wafer. Thus, the invention makes possible a relatively inexpensive instrument for analyzing hidden or latent defects in silicon wafers. Obviously, other material samples can be suitably analyzed for stress, fracture or the like in the manner similar to that described above.

Figure 5:
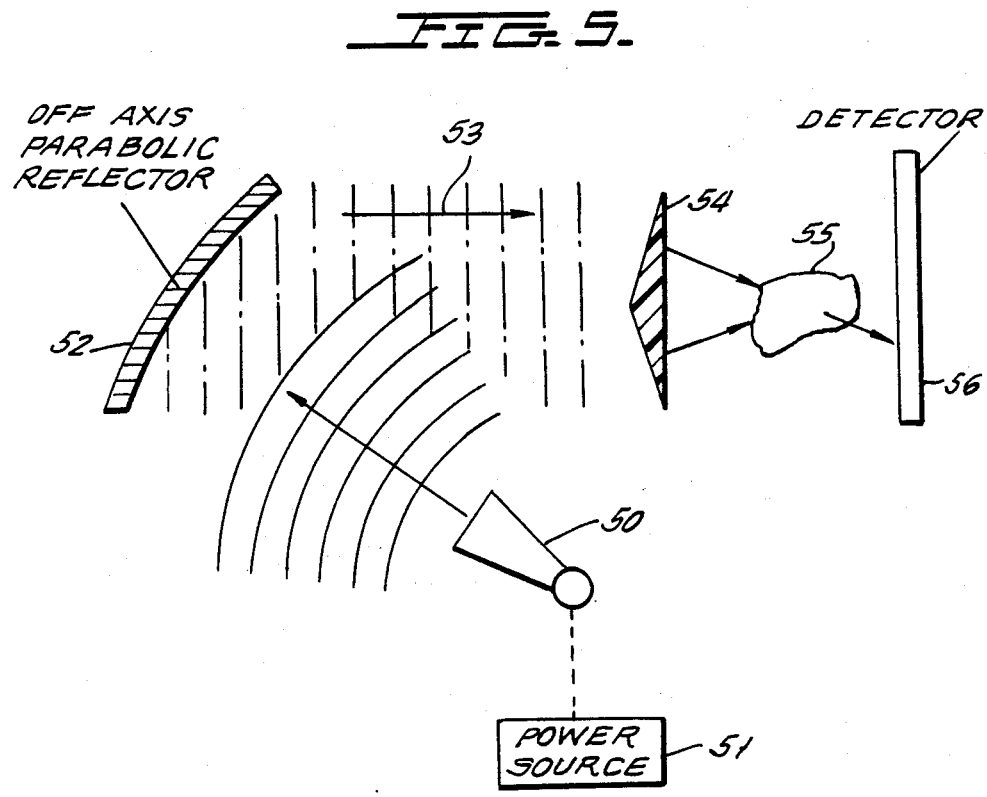
FIG. 5 is a schematic diagram of a third, and preferred embodiment of the invention in which an off-axis parabolic reflector and Fresnel biprism is employed.

A further embodiment of the invention is disclosed in FIG. 5 which shows an improved method for generating an interference field input coherent wave beam with parallel wavefronts. Thus, in FIG. 5, a microwave (millimeter wave) source 50 of conventional form is provided with a driving power source 51. Microwave source or antenna 50 can be operated in the frequency range described in FIG. 1. The output of microwave antenna 50 consists of spherical wave fronts which are applied to an off-axis parabolic microwave reflector 52. By appropriately designing the curvature of the parabolic reflector relative to its spacing from source 50, it is possible to produce planar parallel reflected wave fronts moving in the direction of arrow 53 and toward the Teflon biprism beam separator 54. The converging beams produced by the biprism 54 are then perturbed by the object 55, as described previously. When object 55 can be organic tissue or the like, and the perturbed fringe pattern then detected by detector 56. Note that detector 56 can include means for converting the radiation to visible light and that the perturbed image can then be applied to a ground glass screen and observed or photographed. Optoelectric imaging techniques can also be used.

Figure 6:
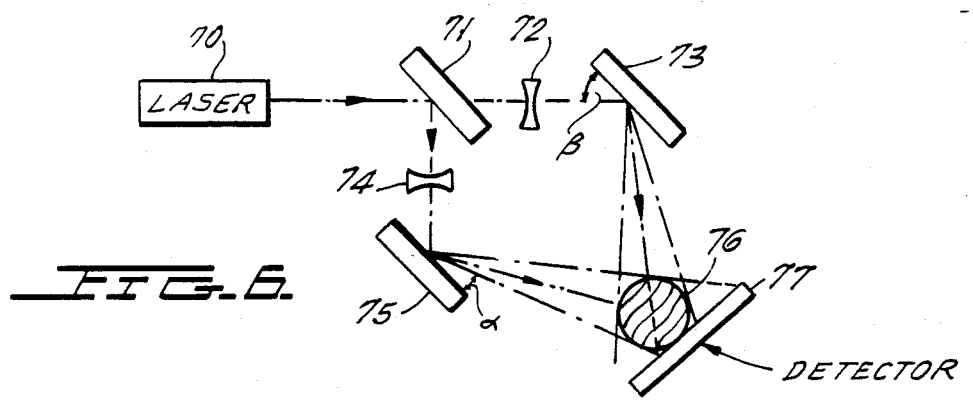
FIG. 6 is a still further embodiment of the present invention in which an interferometer with a low component count is employed as the source of the two coherent radiation beams.

FIG. 6 shows another embodiment of the invention in which an interferometer of low part count is used as the source of the interference field. Thus, in FIG. 7, the output of a laser 70 is applied to a beam splitter 71. The path through beam splitter 71 is applied to a diverging lens 72 and mirror 73, while the other path from mirror 71 proceeds through diverging lens 74 to reflecting mirror 75. The path lengths from mirrors 73 and 74 are of the same length and the radiation from the two paths interfere in the object space, shown as containing an object 76. Detector 77, which may be a camera senstive to the radiation of laser 70, can take a photograph of the interference fringe pattern which is produced with or without object 76 in the object space.

Figure 7:
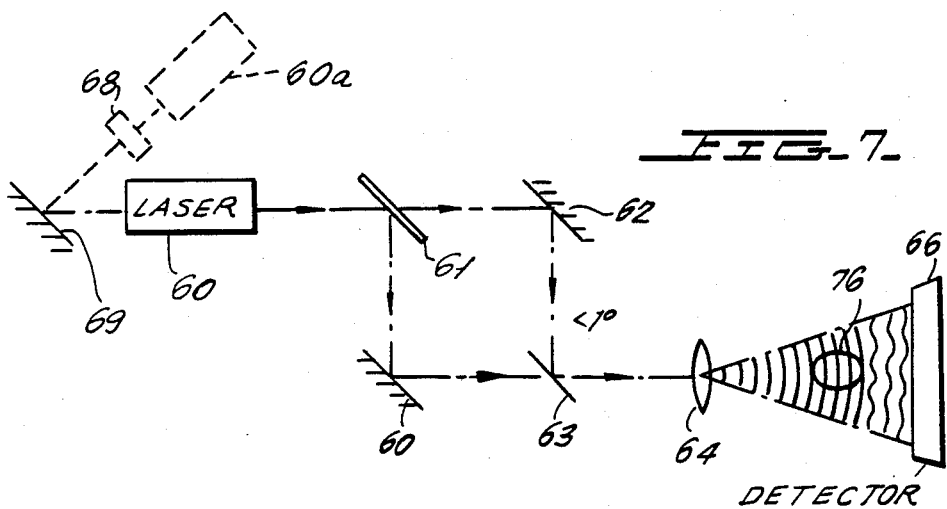
FIG. 7 is a schematic diagram of apparatus having a Mach-Zehnder interferometer which was employed to test the concept of the present invention in which interference fringes with pertubations caused by an object were produced through the interference of two coherent beams.

FIG. 7 shows still another embodiment of the invention in which the convergent beams of coherent radiation are produced by a Mach-Zehnder interferometer. Thus, in FIG. 7, a laser source 60 directs an output beam of light toward beam splitter 61, which divides the beam into two paths which are directed toward reflecting mirrors 62 and 63. These two paths are of identical length and are recombined in a second beam splitter 63. Beam splitter 63 has an angle such that the light from mirror 62 is caused to converge at an angle which is less than about 1° relative to the light coming from mirror 63. These two converging beams are applied to optical lens 64 which can, for example, be a 60 power microscope objective which produces separate converging beams which interfere in the space containing object 76 which is to be examined. As before, the two beams coming from the path containing mirror 62 and from the path containing mirror 63, have their interference patterns perturbed by the object 76 to reveal interior structural characteristics of the object 76. The perturbed fringe pattern is then detected by the detector 66 which may be similar to the detector disclosed in FIG. 4.

An alternate arrangement for FIG. 7 is shown in dotted lines in FIG. 7 where the laser 60a produces an output through an attenuator 68 to a reflector 69 which then produces the output light for use by the Mach-Zehnder interferometer portion of the system.

Figure 8:
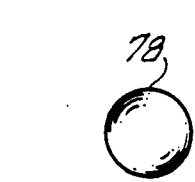
FIG. 8 is a plan view of a circular plastic ball which was used in one experiment in the apparatus of FIG. 7.
Figure 11:
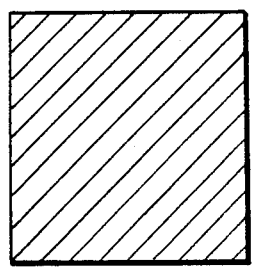
FIG. 11 shows the interference fringe pattern which was observed in the apparatus of FIG. 7 with no object in the object analysis space.
Figure 12:
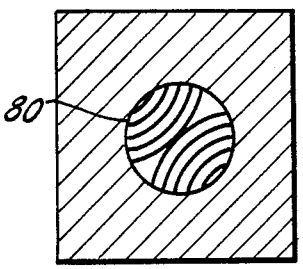
FIG. 12 shows the manner in which the interference fringe pattern of FIG. 11 was perturbed when the object of FIG. 8 was placed in the object analysis space in FIG. 7.

The object 76, in one experiment using the apparatus of FIG. 7, was a simple spherical transparent plastic which was a polymethylmethacrylate (Lucite) ball 78 shown in FIG. 8. Laser 70 was a 4 milliwatt, unpolarized HeNe device. When the ball 78 was not in the object space 76 and the object space was clear, the fringe pattern consisted of straight parallel fringes, as shown in FIG. 11. When, however, the spherical object 78, which was semitransparent to the radiation of laser 70, was in place, the interference pattern of FIG. 12 was observed. In FIG. 12, the circular region 80 was simply the outline of the diameter of the object 78. Note that outside of this circular region, the same unperturbed parallel fringes of FIG. 11 were observed. In the area within the outline 80, however, the fringe pattern consisted of arcuate fringes curving away from one another on the opposite sides of the center of region 80, disclosing the shape of the object and the lack of discontinuities within the object.

Figure 9:
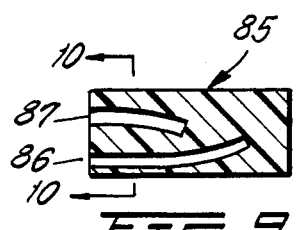
FIG. 9 is a sectional view of FIG. 10, taken across section line 9—9 in FIG. 10, of an elongated cylinder of plastic having two curved openings therein which was employed in another test of the apparatus of FIG. 7.
Figure 10:
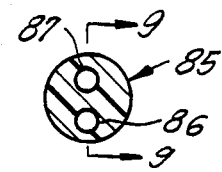
FIG. 10 is a cross-sectional view of the cylinder of FIG. 9 taken across section line 10—10 of FIG. 9.
Figure 13:
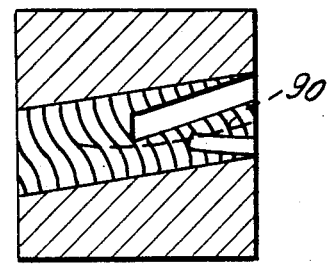
FIG. 13 shows the manner in which the fringe pattern of FIG. 11 was perturbed when the object of FIGS. 9 and 10 was placed in the object analysis space of FIG. 7.

In a second experiment, a Lucite plastic cylinder 85 of FIGS. 9 and 10 was used, in which the plastic cylinder 85 was semi-transparent to the laser radiation and was of the same material of the ball 78. The cylinder 85 contained two arcuate openings 86 and 87 therein which simulated the shape and size of blood carrying vessels. Object 76 was placed in the object space of FIG. 7 with its axis extending parallel to the plane of detector 77. The fringe pattern obtained by placing the object 85 in the object space 76 is shown in FIG. 13. The fringe pattern is unperturbed outside of the outline of the cylinder 85. Within the cylinder 85, however, fringe discontinuities in the regions of the openings 86 and 87 outlined the openings 86 and 87. A stress plane in the plastic which was not visible to the eye was also revealed at dotted line 90.

In the processing of the information which is obtained in the perturbations in the interference pattern produced by the invention, any desired processing can be employed. It is, for example, possible to use non-coherent fourier transform output techniques and then to process these to produce the output image. Similarly it is possible to employ holographic-like reconstruction of the information to produce three-dimensional stress perturbation images of the object being analyzed.

While the above disclosure preferably employs radiation outside of the range of ionizing radiation, it is also possible to employ ionizing radiation. By way of example, it is possible to incorporate an x-ray band using "K" edge absorption concepts. This has been used in x-ray interferometry at energies less than about 10 KEV and can be extended to application with the present invention.

Although the present invention has been described in connection with a preferred embodiment thereof, many variations and modifications will now become apparent to those skilled in the art. It is preferred, therefore, that the present invention be limited not by the specific disclosure herein, but only by the appended claims.

What is claimed is:

1. The process of examining an object comprising the steps of directing first and second beams of coherent radiation of a frequency at which said object is transparent toward said object so that said beams interfere with one another, whereby the interference pattern which is produced is distorted from the pattern which would be produced in the absence of said object, and thereafter deducing from the pattern at least one characteristic of said object.

2. The process of claim 1, wherein said object is a living organism.

3. The process of claim 1 or 2 which further includes the step of varying or sweeping the frequency of said coherent radiation through the absorption band frequency of at least one chemical element which is present in said object and analyzing the distortion produced at said absorption band frequency.

4. The process of claim 3, wherein said radiation is in the millimeter radiation band and wherein said radiation is produced in short, spaced pulses to avoid unnecessary heating of said object.

5. The process of claim 3, wherein said radiation frequency is one of microwave, visible, ultraviolet and x-ray frequencies.

6. The process of claim 1, wherein said object is a semiconductor silicon wafer.

7. The process of claim 1, wherein said radiation frequency is one of microwave, visible, ultraviolet and x-ray frequencies.

8. Apparatus for analyzing selected characteristics of a sample; said apparatus comprising:
   means for supporting said sample in an object space;
   means for producing two coherent interfering beams of radiation of the same frequency which pass through said specimen sample;
   said beams being of a frequency to which at least portions of said sample are semitransparent and refractive, whereby the interference fringes produced by said beam are perturbed;
   detector means positioned on the side of said sample at which said beams exit from said sample from which fringe information can be derived.

9. The apparatus of claim 8, wherein said beams have a wavelength in the millimeter range.

10. The apparatus of claim 8, wherein said beams have a wavelength in the range containing infrared, visible and ultraviolet light.

11. The apparatus of claim 8, which includes means for varying the frequency of said beams over a band which is greater than about 5 gigahertz and less than about 500 gigahertz.

12. The apparatus of claim 11, wherein said means for varying the frequency steps said frequency over a given number of different discrete frequencies.

13. The apparatus of claim 8 or 11 which further includes means for stabilizing the temperature of said apparatus.

* * * * *